United States Patent
Chavan et al.

(10) Patent No.: US 8,433,404 B2
(45) Date of Patent: Apr. 30, 2013

(54) INTEGRATED HIGH VOLTAGE OUTPUT CIRCUIT

(75) Inventors: Abhi V. Chavan, Maple Grove, MN (US); Keith R. Maile, New Brighton, MN (US); Andrew Bartczak, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 172 days.

(21) Appl. No.: 12/762,753

(22) Filed: Apr. 19, 2010

(65) Prior Publication Data

US 2010/0298897 A1    Nov. 25, 2010

Related U.S. Application Data

(60) Provisional application No. 61/179,520, filed on May 19, 2009.

(51) Int. Cl.
*A61N 1/39* (2006.01)
(52) U.S. Cl.
USPC .............................................................. 607/4
(58) Field of Classification Search ................. 607/4, 5
See application file for complete search history.

(56) References Cited

U.S. PATENT DOCUMENTS

| | | | |
|---|---|---|---|
| 4,599,523 A | 7/1986 | Pless et al. | |
| 4,800,883 A | 1/1989 | Winstrom | |
| 4,998,531 A | 3/1991 | Bocchi et al. | |
| 5,033,467 A | 7/1991 | Bocchi et al. | |
| 5,251,624 A | 10/1993 | Bocek et al. | |
| 5,385,575 A * | 1/1995 | Adams | 607/5 |
| 5,447,522 A | 9/1995 | Chang et al. | |
| 5,540,724 A | 7/1996 | Cox | |
| 5,591,211 A | 1/1997 | Meltzer | |
| 5,591,212 A | 1/1997 | Keimel | |
| 5,645,572 A | 7/1997 | Kroll et al. | |

(Continued)

FOREIGN PATENT DOCUMENTS

| | | |
|---|---|---|
| EP | 1530983 A2 | 5/2005 |
| EP | 1535645 A1 | 6/2005 |

(Continued)

OTHER PUBLICATIONS

"International Application Serial No. PCT/US2008/013616, International Search Report mailed Jun. 17, 2009", 5 pgs.

(Continued)

*Primary Examiner* — George Evanisko
(74) *Attorney, Agent, or Firm* — Schwegman Lundberg & Woessner, P.A.

(57) ABSTRACT

An apparatus includes a cardioversion or defibrillation therapy energy source coupled to a bridge circuit. The bridge circuit includes a first switch for connection to a first implantable electrode, a second switch for connection to a second implantable electrode, a third switch coupled for connection to the first implantable electrode, and a fourth switch coupled for connection to the second implantable electrode. The first and second switches are formed on a shared first IC, the third and fourth switches are formed on a shared second IC, and the second IC is stacked substantially superjacent to the first IC such that a cathode of the first switch is coupled to an anode of the third switch and a cathode of the second switch is coupled to an anode of the fourth switch.

22 Claims, 6 Drawing Sheets

U.S. PATENT DOCUMENTS

| | | |
|---|---|---|
| 5,693,952 A | 12/1997 | Cox |
| 5,720,767 A | 2/1998 | Amely-Velez |
| 5,723,969 A | 3/1998 | Archer et al. |
| 5,733,309 A | 3/1998 | Kroll et al. |
| 5,745,350 A | 4/1998 | Archer et al. |
| 5,772,689 A | 6/1998 | Kroll |
| 5,800,461 A | 9/1998 | Menken et al. |
| 5,817,130 A | 10/1998 | Cox et al. |
| 5,830,236 A | 11/1998 | Mouchawar et al. |
| 5,836,971 A | 11/1998 | Starkweather |
| 5,836,983 A | 11/1998 | Weijand et al. |
| 5,954,751 A * | 9/1999 | Chen et al. .......... 607/5 |
| 5,968,083 A | 10/1999 | Ciciarelli et al. |
| 5,991,211 A | 11/1999 | Kato |
| 6,014,586 A * | 1/2000 | Weinberg et al. ....... 607/36 |
| 6,026,325 A * | 2/2000 | Weinberg et al. ....... 607/36 |
| 6,035,235 A * | 3/2000 | Perttu et al. .......... 607/5 |
| 6,175,765 B1 | 1/2001 | Sullivan et al. |
| 6,233,483 B1 | 5/2001 | Causey, III et al. |
| 6,311,087 B1 | 10/2001 | Vane et al. |
| 6,421,563 B1 | 7/2002 | Sullivan et al. |
| 6,438,420 B1 | 8/2002 | Thompson |
| 6,456,877 B1 | 9/2002 | Fishler |
| 6,477,413 B1 | 11/2002 | Sullivan et al. |
| 6,484,056 B2 | 11/2002 | Fisher et al. |
| 6,505,072 B1 | 1/2003 | Linder et al. |
| 6,522,920 B2 | 2/2003 | Silvian et al. |
| 6,539,258 B1 | 3/2003 | Sullivan et al. |
| 6,647,294 B2 | 11/2003 | Vane et al. |
| 6,650,942 B2 | 11/2003 | Howard et al. |
| 6,668,193 B2 | 12/2003 | Ware et al. |
| 6,714,818 B1 | 3/2004 | Fishler et al. |
| 6,745,073 B1 | 6/2004 | Kroll |
| 6,763,266 B1 | 7/2004 | Kroll |
| 6,772,007 B1 | 8/2004 | Kroll |
| 6,873,874 B2 | 3/2005 | Ware et al. |
| 6,954,669 B1 | 10/2005 | Fishler et al. |
| 6,963,773 B2 | 11/2005 | Waltman et al. |
| 6,968,230 B2 | 11/2005 | Waltman |
| 6,968,231 B1 | 11/2005 | Silvian et al. |
| 6,980,856 B2 | 12/2005 | Sullivan et al. |
| 6,991,961 B2 | 1/2006 | Hubbard et al. |
| 7,069,075 B2 | 6/2006 | Olson |
| 7,096,063 B2 * | 8/2006 | Wanasek et al. ......... 607/5 |
| 7,139,606 B2 | 11/2006 | Vane et al. |
| 7,151,963 B2 | 12/2006 | Havel et al. |
| 7,155,286 B1 | 12/2006 | Kroll et al. |
| 7,383,085 B2 | 6/2008 | Olson |
| 8,116,865 B2 | 2/2012 | Linder et al. |
| 8,125,071 B2 * | 2/2012 | Kuan ............. 257/690 |
| 2004/0172066 A1 | 9/2004 | Wagner et al. |
| 2004/0254613 A1 | 12/2004 | Ostroff et al. |
| 2005/0165451 A1 | 7/2005 | Ware et al. |
| 2009/0157132 A1 | 6/2009 | Linder et al. |
| 2012/0143274 A1 | 6/2012 | Linder et al. |

FOREIGN PATENT DOCUMENTS

| | | |
|---|---|---|
| WO | WO-9503087 A1 | 2/1995 |
| WO | WO-2005092437 A1 | 10/2005 |
| WO | WO-2009078942 A2 | 6/2009 |
| WO | WO-2009078942 A3 | 6/2009 |

OTHER PUBLICATIONS

"International Application Serial No. PCT/US2008/013616, Written Opinion mailed Jun. 17, 2009", 8 pgs.

"U.S. Appl. No. 12/332,497, Non-Final Office Action mailed Jun. 13, 2011", 9 pgs.

"U.S. Appl. No. 12/332,497, Notice of Allowance mailed Oct. 11, 2011", 7 pgs.

"U.S. Appl. No. 12/332,497, Response filed May 4, 2011 to Restriction Requirement mailed Apr. 8, 2011", 9 pgs.

"U.S. Appl. No. 12/332,497, Response filed Sep. 13, 2011 to Non-Final Office Action mailed Jun. 13, 2011", 17 pgs.

"U.S. Appl. No. 12/332,497, Restriction Requirement mailed Apr. 8, 2011", 6 pgs.

* cited by examiner

INTEGRATED HIGH VOLTAGE OUTPUT CIRCUIT

CROSS REFERENCE TO RELATED APPLICATION

Benefit of priority is hereby claimed to U.S. Provisional Patent Application Ser. No. 61/179,520, filed on May 19, 2009, the specification of which is herein incorporated by reference in its entirety.

TECHNICAL FIELD

This patent application pertains generally to implantable cardiac rhythm management devices and more particularly, but not by way of limitation, to a programmable output energy delivery bridge.

BACKGROUND

Implantable medical devices include, among other things, cardiac function management (CFM) devices such as pacers, cardioverters, defibrillators, cardiac resynchronization therapy (CRT) devices, as well as combination devices that provide more than one of these therapy modalities to a subject. For example, an implantable defibrillator/pacer is typically configured as an implantable defibrillator with backup pacing capability. Such devices are intended to serve patients having a history of previous ventricular or atrial tachyarrhythmia episodes. Ventricular arrhythmias include ventricular tachyarrhythmia (VT) and dangerous and life-threatening ventricular fibrillation (VF), referred to collectively herein as VT/VF. VT/VF is typically treated with antitachyarrhythmia pacing (ATP) therapy or a defibrillation countershock. Because of the voltages involved in the countershock, a solid state output circuits that deliver the countershock therapy can be difficult and expensive to implement.

OVERVIEW

This document discusses examples of techniques for generating and delivering a high voltage defibrillation shock using an implantable CFM device and to techniques for forming output circuits to deliver the high voltage defibrillation shock.

In example 1, a method includes a cardioversion or defibrillation therapy energy source coupled to a first node, and a bridge circuit coupled to the first node and a second node. The bridge circuit includes: a first switch coupled to the first node and a third node configured to be communicatively coupled to a first implantable electrode sized and shaped for providing defibrillation or cardioversion therapy, a second switch coupled to the first node and a fourth node configured to be communicatively coupled to a second implantable electrode sized and shaped for providing defibrillation or cardioversion therapy, a third switch coupled to the third node and the second node, and a fourth switch coupled to the fourth node and the second node. The first and second switches are formed on a shared first integrated circuit, the third and fourth switches are formed on a shared second integrated circuit, and the second integrated circuit is stacked substantially superjacent to the first integrated circuit such that a cathode of the first switch is coupled to an anode of the third switch and a cathode of the second switch is coupled to an anode of the fourth switch.

In example 2, the first and second integrated circuits of example 1 optionally include high voltage electrical isolation structures between adjacent edges of the switches and at non-adjacent edges of the switches, and wherein the isolation structures between the adjacent edges are formed thinner than the isolation structures formed at the non-adjacent edges.

In example 3, the isolation structures at the non-adjacent edges of any one or more of examples 1 and 2 optionally include a thickness sufficient to accommodate sawing of the first and second integrated circuits.

In example 4, the isolation structures of any one or more of examples 1-3 are optionally formed using aluminum column diffusion.

In example 5, the isolation structures of any one or more of examples 1-4 are optionally formed using deep reactive ion etching.

In example 6, the energy source of any one or more of examples 1-5 optionally includes a capacitor, the first and second switches optionally include remote gate thyristors (RGTs), and the third and fourth switches optionally include silicon controlled rectifiers (SCRs).

In example 7, the apparatus of any one or more of examples 1-6 optionally includes a fifth switch coupled to the first node and a fifth node, and a sixth switch coupled to the fifth node and the second node. The fifth node is configured to be communicatively coupled to a third implantable electrode sized and shaped for defibrillation or cardioversion therapy. The fifth switch is included in the first integrated circuit and the sixth switch is included in the second integrated circuit.

In example 8, the first implantable electrode of any one or more of examples 1-7 is optionally configured for placement in or near an atrium, the second implantable electrode is optionally configured for placement in or near a ventricle, and the third implantable electrode of example 7 optionally includes an electrode formed on a housing of the apparatus.

In example 9, the second implantable electrode of any one or more of examples 1-8 is optionally configured for placement in or near a left ventricle.

In example 10, the first and second switches of any one or more of examples 1-9, and the fifth switch of any one or more of examples 7-9, optionally include a gate connection, and each gate connection is coupled to a field effect transistor (FET).

In example 11, the apparatus of any one or more of examples 1-10 optionally includes a seventh switch coupled between the therapy energy source and the first node, wherein the seventh switch provides the therapy energy to the bridge circuit.

In example 12, the seventh switch of example 11 optionally includes an insulated gate bipolar transistor (IGBT), and the apparatus includes an enable circuit coupled to the IGBT.

In example 13 a method example includes stacking a first integrated circuit substantially superjacent to a second integrated circuit. The first integrated circuit includes a first switch and a second switch and the second integrated circuit includes a third switch and a fourth switch. The method further includes coupling a cathode of the first switch to an anode of the third switch and coupling a cathode of the second switch to an anode of the fourth switch, coupling the cathode of the first switch to a first node configured to be communicatively coupled to a first implantable electrode sized and shaped for defibrillation or cardioversion therapy, coupling the cathode of the second switch to a second node configured to be communicatively coupled to a second implantable electrode sized and shaped for defibrillation or cardioversion therapy, and coupling the anodes of the first and second switches to a third node. A cardioversion or defibrillation therapy energy source is coupled to the third node.

In example 14, the method of example 13 optionally includes forming high voltage electrical isolation structures in the first and second integrated circuits between adjacent edges of the switches and at non-adjacent edges of the switches, such that the isolation structures between the adjacent edges are thinner than isolation structures formed at the non-adjacent edges.

In example 15, the forming isolation structures at the non-adjacent edges of example 14 optionally includes forming isolation structures at the non-adjacent edges that are wide enough to accommodate sawing of the first and second integrated circuits.

In example 16, the forming isolation structures of any one or more of examples 14 and 15 optionally includes forming isolation structures using aluminum column diffusion.

In example 17, the forming isolation structures of any one or more of examples 14-16 optionally includes forming isolation structures using deep reactive ion etching.

In example 18, the coupling the energy source of any one or more examples 13-18 optionally includes coupling a capacitor to the third node, wherein the capacitor is configured to store sufficient charge to provide the cardioversion or defibrillation therapy, and the stacking first and second integrated circuits optionally includes stacking a first integrated circuit including remote gate thyristors (RGTs) and stacking a second integrated circuit including silicon controlled rectifiers (SCRs).

In example 19, the method of any or more of examples 13-18 optionally includes coupling a cathode of a fifth switch to an anode of a sixth switch, wherein the fifth switch is included in the first integrated circuit and the sixth switch is included in the second integrated circuit, and coupling a fourth node to the cathode of the fifth switch, wherein the fourth node is configured to be communicatively coupled to a third implantable electrode sized and shaped for defibrillation or cardioversion therapy.

In example 20, the coupling a first node to the cathode of the first switch of any one or more of examples 13-19 optionally includes coupling the cathode of the first switch to a node to be communicatively coupled to a first implantable electrode sized and shaped for placement in or near an atrium, the coupling a second node to the cathode of the second switch optionally includes coupling the cathode of the second switch to a node to be communicatively coupled to a second implantable electrode sized and shaped for placement in or near a ventricle, and the coupling a fourth node to the cathode of the fifth switch of example 19 optionally includes coupling the cathode to a node to be communicatively coupled to an electrode formed on a housing of the apparatus.

In example 21, the method of examples 13-20 optionally includes coupling a seventh switch between the therapy energy source and the third node to control delivery of therapy energy to the third node.

In example 22, an apparatus example includes a cardioversion or defibrillation therapy energy source coupled to a first node and a bridge circuit coupled to the first node and a second node. The bridge circuit includes a first high voltage switch coupled to the first node and a third node configured to be communicatively coupled to a first implantable electrode sized and shaped for defibrillation or cardioversion therapy, a second high voltage switch coupled to the first node and a fourth node configured to be communicatively coupled to a second implantable electrode sized and shaped for defibrillation or cardioversion therapy, a third high voltage switch coupled to the third node and the second node, and a fourth high voltage switch coupled to the fourth node and the second node. The first, second, third, and fourth high voltage switches are formed on a single shared integrated circuit such that a cathode of the first high voltage switch is coupled to an anode of the third high voltage switch and a cathode of the second high voltage switch is coupled to an anode of the fourth high voltage switch.

In example 23, the integrated circuit includes high voltage electrical isolation structures between adjacent edges of the high voltage switches and at non-adjacent edges of the high voltage switches, and the integrated circuit is formed with isolation structures between the adjacent edges that are thinner than isolation structures formed at the non-adjacent edges.

In example 24, the isolation structures of example 23 are optionally formed using aluminum column diffusion, and the isolation structures at the non-adjacent edges include a thickness sufficient to accommodate sawing of the integrated circuit.

In example 25, the isolation structures of any one or more of examples 24 and 25 are formed using deep reactive ion etching.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document discusses systems and methods for providing high voltage cardioversion or defibrillation therapy to patient or subject. Specifically, systems including a high voltage output circuit are described.

An implantable medical device (IMD) may include one or more of the features, structures, methods, or combinations thereof described herein. For example, a cardiac stimulator may be implemented to include one or more of the advantageous features or processes described below. It is intended that such a stimulator or other implantable or partially implantable device need not include all of the features described herein, but may be implemented to include selected features that provide for unique structures or functionality. Such a device may be implemented to provide a variety of therapeutic or diagnostic functions.

Figure 1:
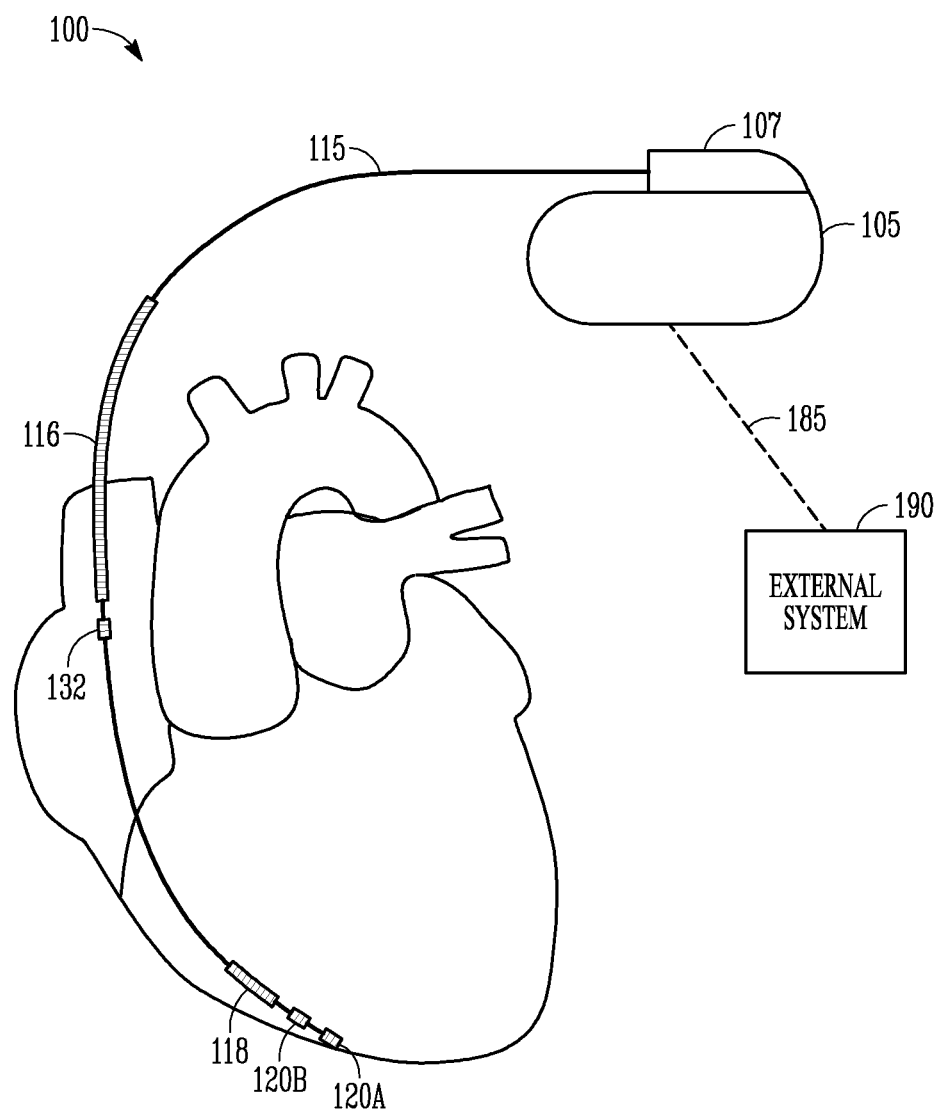
FIG. 1 is an illustration of an example of portions of a system that includes a CFM device capable of providing one or both of cardioversion and defibrillation therapy.

FIG. 1 is an illustration of an example of portions of a system 100 that includes an IMD 105. Examples of IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD 105 includes a sense amplifier circuit to provide amplification or filtering of the sensed signal. Sensing and pacing allows the IMD 105 to adjust timing of the heart chamber contractions.

Figure 2:
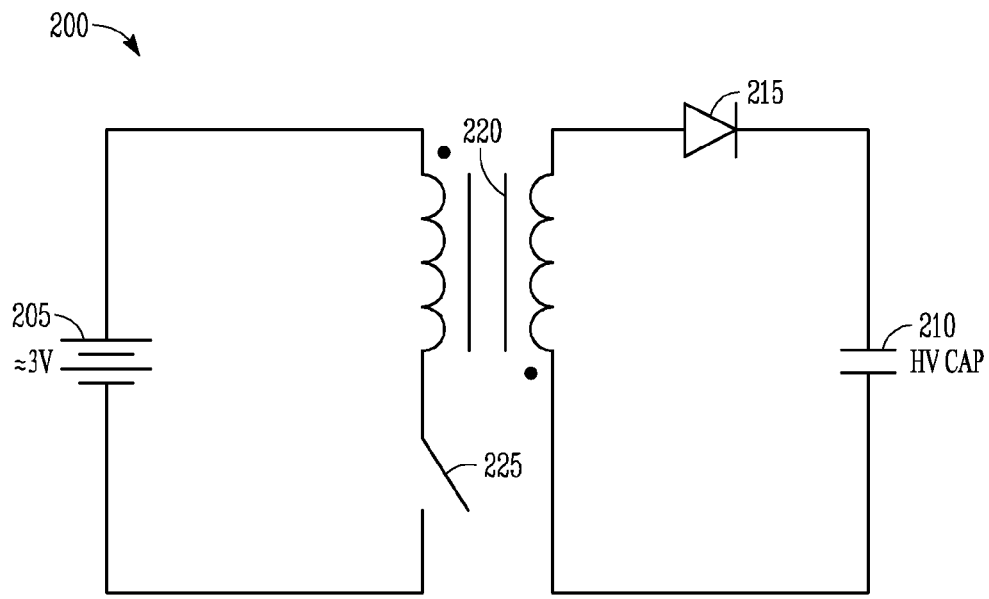
FIG. 2 is an example of a high voltage charging circuit for generating a high defibrillation or cardioversion voltage in an implantable CFM device.

FIG. 2 is an example of a high voltage charging circuit 200 for generating a high cardioversion or defibrillation voltage (e.g., 40V-780V) in an IMD such as an implantable cardioverter/defibrillator (ICD). In this example, the high cardioversion or defibrillation voltage is stored on at least one high voltage capacitor 210 ("HV Cap"), and the HV Cap is the energy source for cardioversion or defibrillation therapy to be delivered by the IMD. The particular stored voltage depends on the desired shock energy (e.g., 0.1 J to 41 J). FIG. 2 shows an example of how this can be accomplished by using a flyback converter to transfer energy from the battery 205 (e.g., at about 3V) to the HV Cap.

In FIG. 2, when the switch 225 (e.g., n-channel MOSFET) is closed, the current through the primary winding of the flyback transformer ramps up to a maximum value (e.g., about 9 amps). While this current is building, the diode 215 is reverse-biased, so no current flows in the secondary winding of the transformer 220. When the current reaches its desired peak value, the switch 225 is opened. When the switch 225 is opened, the output of the transformer 220 reverses and the diode 215 becomes forward biased. The energy that was stored in the transformer 220 is then transferred to the HV Cap. This can be repeated (e.g., at 10 microsecond cycles) until the HV Cap is charged to the desired voltage.

In certain examples, one or more bypass capacitors can be placed in parallel with the battery 205 to help source the peak current when the switch 225 is closed. In certain examples, the HV Cap can be implemented as two separate capacitors in series, and each such series capacitor can be given its own secondary transformer winding. In certain examples, additional transformer windings can be used, such as to supply the current used to meet the current demands associated with switching the switch in the primary winding path.

Figure 3:
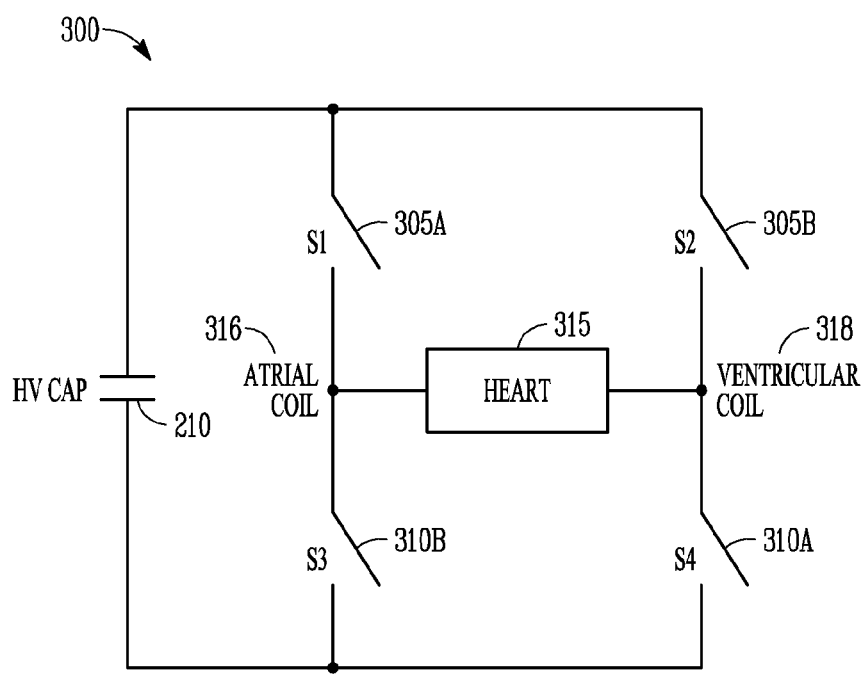
FIG. 3 is a drawing of an example of an H-bridge output bridge approach for delivering energy from a cardioversion or defibrillation energy therapy source to defibrillation electrodes.

FIG. 3 is a schematic drawing of an example of an H-bridge output bridge circuit 300 approach for delivering energy from a cardioversion or defibrillation energy therapy source such as an HV Cap to the desired defibrillation electrodes, which are implanted within the patient receiving the defibrillation therapy. Examples of such defibrillation electrodes are denoted as "atrial coil" 316 and "ventricular coil" 318 in FIG. 3. Switches 305A, 305B, 310A, 310B are high voltage switches able to withstand the voltage and current of the therapy energy. A top ("high side") switch may be implemented as a thyristor (e.g., a remote gate thyristor (RGT) or a TRIAC), and a bottom switch may be implemented as field effect transistor (FET) or a silicon controller rectifier (SCR).

If it is desired that the atrial coil 316 be positive during a first phase of a two-phase (biphasic) defibrillation waveform, then the switches labeled 305A and 310A can be closed for phase 1. After phase 1, the switches labeled 305A and 310A can be opened. Then, the switches labeled 305B and 310B can be closed for phase 2, and then opened after phase 2. In a "hot can" configuration, the implantable defibrillator housing (which is sometimes referred to as the "can") provides a "can" electrode that is electrically connected (e.g., "shorted") to the atrial coil electrode 316. This can be accomplished, in certain examples, via a hard electrical connection (e.g., provided at manufacturing) in a header feed-through portion of the implantable defibrillator, where the atrial and ventricular coil electrodes are disposed on an intravascular leadwire that is electrically connected to the implantable defibrillator at the header. In a "cold can" configuration, the implantable defibrillator housing is not electrically connected to the atrial or ventricular coil electrodes.

Figure 4:
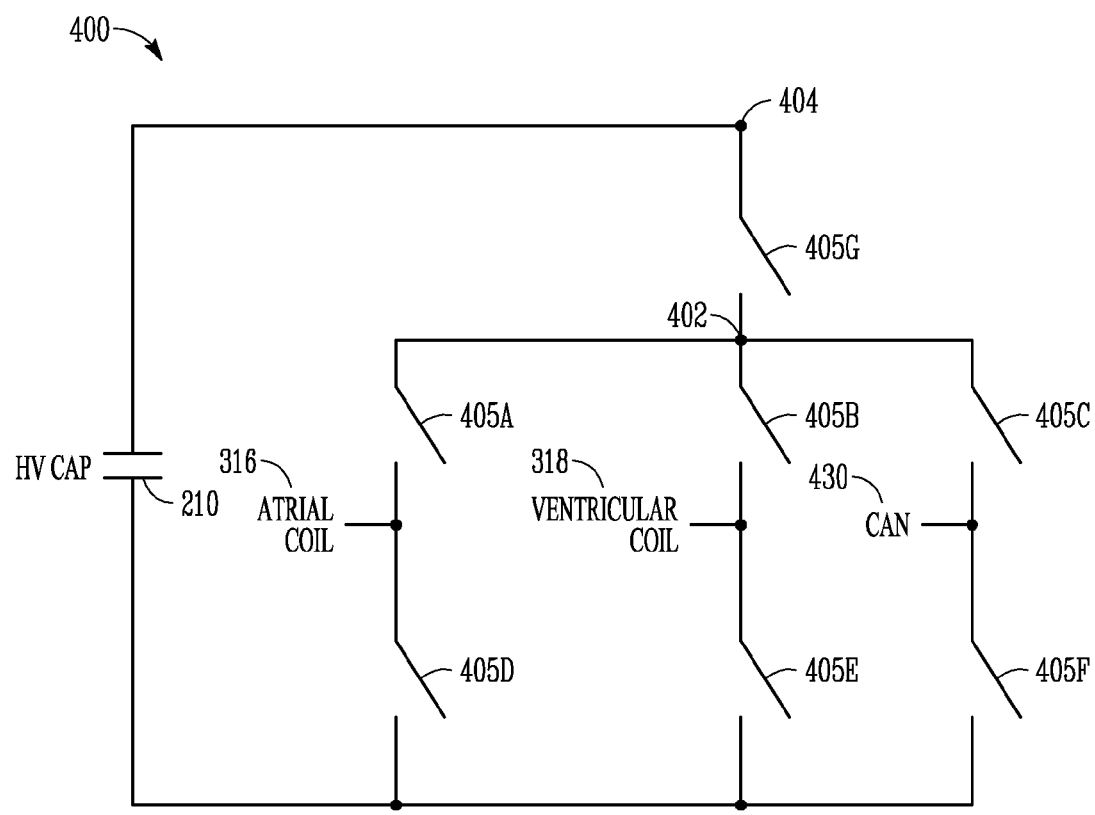
FIG. 4 is a schematic drawing of an example of an alternative output bridge circuit for delivering energy from the therapy energy source to defibrillation electrodes.

FIG. 4 is a schematic drawing of an example of an alternative output bridge circuit 400 for delivering energy from the therapy energy source to the desired defibrillation electrodes, which are implanted within the patient receiving the defibrillation therapy. Examples of such defibrillation electrodes are denoted as "atrial coil 316," "ventricular coil 318," and "can 430" in FIG. 3. Unlike the hot can example described above with respect to FIG. 3, in the example of FIG. 4, the can electrode 430 can be selectively used (via switches 405C and 405F) rather than being electrically connected or not connected by forming a hard electrical connection at the time of manufacturing the IMD.

The output bridge circuit 400 can be used to provide at least three different defibrillation shock vectors: (1) Right Ventricular Coil 318 to Right Atrial Coil 316; (2) Right Ventricular Coil 318 to Right Atrial Coil 316 and Can 430; or (3) Right Ventricular Coil 318 to Can 430. An example of such shock vectors and corresponding switching configurations is described in Table 1. The CFM may include a defibrillation electrode shaped and sized for placement in or near a left ventricle. For example, Right Atrial Coil 316 may be replaced with a Left Ventricular Coil. In this case the defibrillation shock vectors may include: (1) Left Ventricular Coil to Right Ventricular Coil 318; (2) Right Ventricular Coil 318 to Left Ventricular Coil and Can 430; or (3) Left Ventricular Coil to Can 430.

In certain examples, when a defibrillation shock is delivered, switches 405A-F are configured as desired at a brief time period (e.g., 250 microseconds) before closing switch 405G to provide therapy energy from the therapy energy source to the output bridge circuit 400.

TABLE 1

Example of Shock Vectors and Switch Operation

| Shock Vector | Switches closed during phase 1 | Switches closed during phase 2 |
|---|---|---|
| RV coil to RA coil | 405A, E, G | 405B, D, G |
| RV coil to RA coil and CAN | 405A, C, E, G | 405B, D, F, G |
| RV coil to CAN | 405C, E, G | 405B, F, G |

Figure 5:
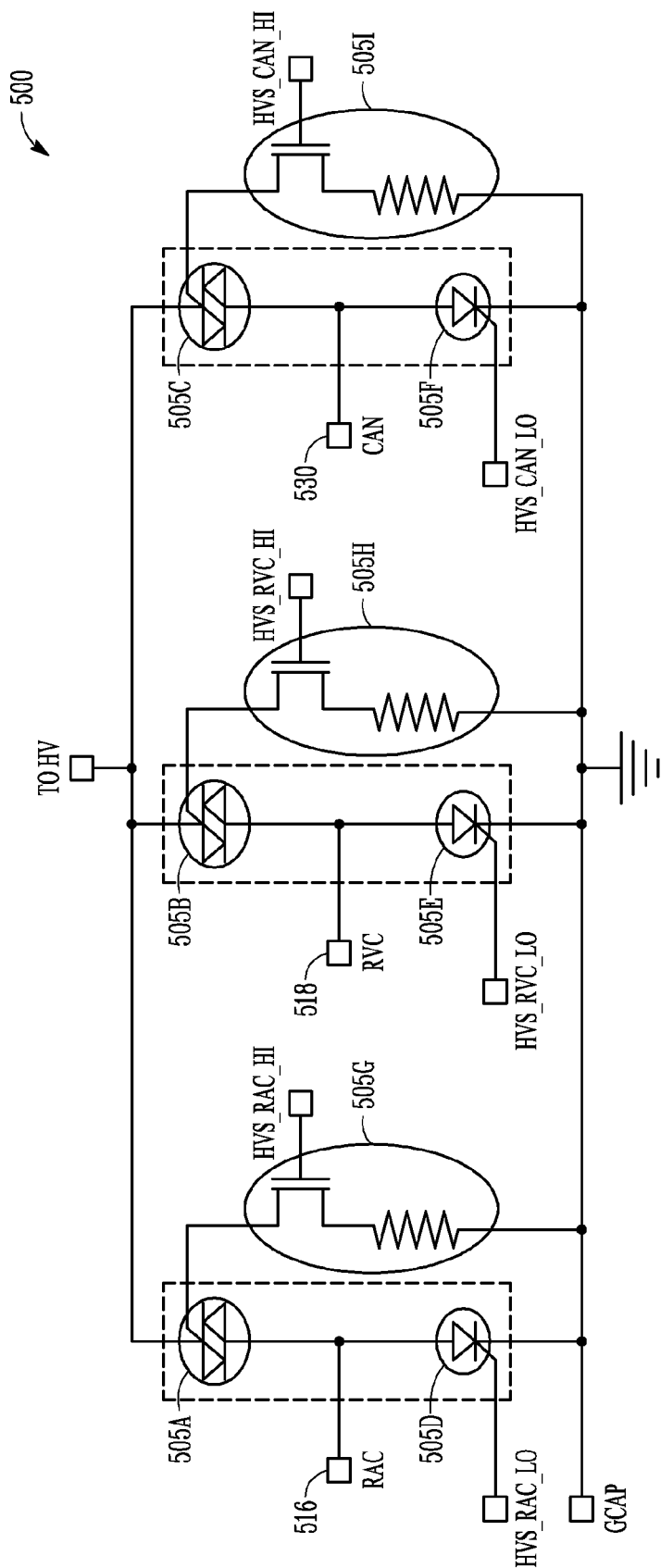
FIG. 5 is a schematic drawing of another example of an output bridge circuit.

FIG. 5 is a schematic drawing of another example of an output bridge circuit 500. The top or high side switches 505A-C are implemented as thyristors (e.g., RGTs), and the bottom or low side switches are implemented as SCRs. The thyristors have a switch connected to the thyristor gate to enable the thyristor. In certain examples, the switches include FETs 505G, 505H, 505I, and the FETs enable the thyristors when the FET gate inputs are high.

The topology of a bridge circuit makes it desirable to integrate two or more of the switches into a single integrated circuit (IC) or die. Grouping the switches into die saves space and ultimately reduces the size of the IMD.

In some examples, the switches are integrated into two ICs. The top switches are formed on a first die and the bottom switches are formed on a second die. For the output bridge circuit 300 in FIG. 3, top switches 305A and 305B are formed on the first die, and bottom switches 310A and 310B are formed on the second die. For the output bridge circuit 500 in FIG. 5, top switches 505A, 505B, and 505C are formed on the first die and bottom switches 505D, 505E, and 505F are formed on the second die. Integrating all of the top switches and integrating all of the bottom switches may simplify the circuit interconnect because the integrated switches all share one node (e.g., a connection to the high voltage for the top switches and a connection to a low voltage or ground for the bottom switches).

Figure 6A:
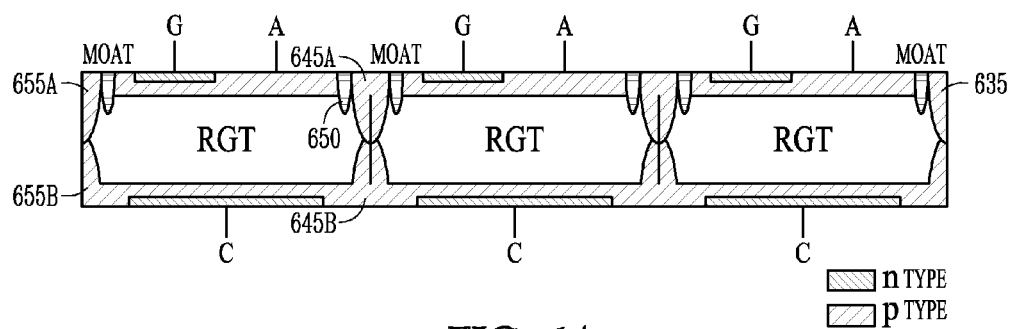
FIGS. 6A and 6B are illustrations of a cross-section of examples of the switches integrated into two die.
Figure 6B:
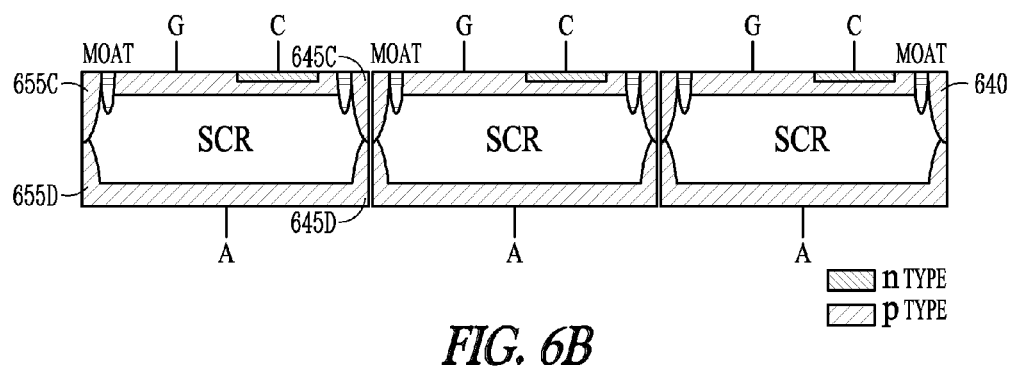

FIGS. 6A and 6B are illustrations of a cross-section of examples of the switches integrated into two die. The die 635 in FIG. 6A includes three top switches that are RGTs and the second die in FIG. 6B includes three bottom switches that are SCRs. Each of the RGTs and SCRs include a cathode (C), an anode (A), and a gate (G). For the RGTs, the gate and cathode are formed from n-type material, and the anode is formed from p-type material. For the SCRs, the cathode is formed from n-type material, and the gate and anode are formed from p-type material.

Because of the voltage levels involved in cardioversion and defibrillation, high voltage switches used in defibrillation circuits typically are formed as separate die. This is done to provide the isolation necessary to prevent crosstalk between the switches. In the typical process, multiple switches are formed on a wafer. Isolation is provided between the die that has a thickness or width sufficient to accommodate sawing between the die. The wafer is then cut into individual die containing one high voltage switch.

In the die of FIGS. 6A and 6B, through-wafer isolation is formed between the switches that is sufficient to remove crosstalk. This high voltage isolation eliminates the need to separate all of the switches into individual die. In some examples, the through-wafer isolation includes aluminum column diffusion. FIG. 6A shows an aluminum column diffusion isolation structure 645A, 645B for the RGTs, and FIG. 6B shows an aluminum column diffusion isolation structure 645C, 645D for the SCRs. Aluminum is used in the diffusion because there is less diffusion in the lateral direction than with a typical diffusion material such as boron for example. The diffusion is begun from both the top of the wafer and the bottom of the wafer and the diffusion meets in the middle to form the aluminum column diffusion isolation structure 645A, 645B. Because the diffusion is begun on the two surfaces and meets in the middle, the diffusion has the hour glass shape shown.

The aluminum diffusion has the advantage of providing the necessary diffusion in the vertical direction while providing a thinner isolation structure between switches. In certain examples, a thicker diffusion isolation structure 655A, 655B (and 655C, 655D) that is wide enough to accommodate sawing is provided at the outside ends of the end switches. Thus, the high voltage isolation structure between the adjacent edges of the switches is formed thinner than the high voltage isolation structure formed at the non-adjacent edges. The thinner isolation structures allow more die to be formed on a wafer, thereby reducing the cost per switch. Also, because not every edge is sawed, integrating the switches has the advantage of less handling of the die which may lead to higher yields. Further, because there is less sawing there is less opportunity to form nicks at the narrowest point of the isolation structure from the sawing. The nicks compromise the isolation and are flaws in the die. Thus, reducing sawing reduces the number of flaws produced in the process, thereby increasing yield.

In certain examples, a moat 650 of insulating material is also formed between switches. In certain examples, the insulating material for the moat is silicon dioxide ($SiO_2$).

In some examples, the isolation structures are formed using deep reactive ion etching (DRIE). DRIE is an etching process used to create deep sided trenches in wafers. Trenches formed by DRIE typically have highly vertical sidewalls. The trenches are then filled with insulating material to form the isolation structures between switches with minimum lateral diffusion. Use of DRIE provides improved control of forming the isolation structures than diffusion-based processes. This allows for more efficient use of die area.

Figure 7:
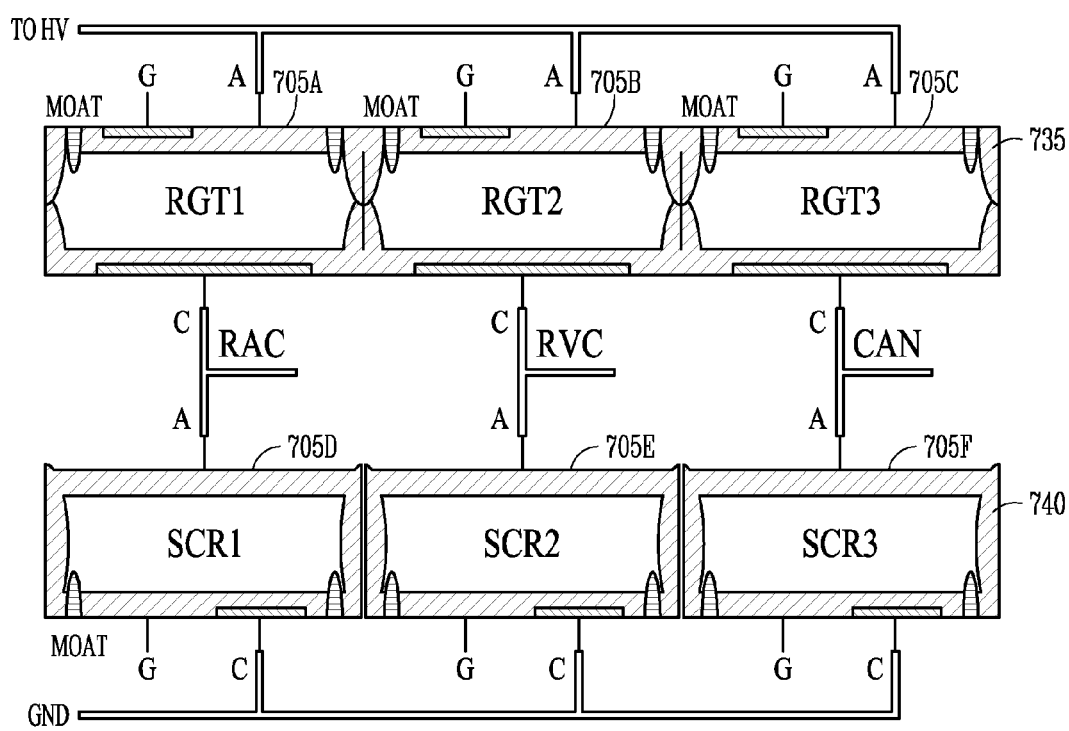
FIG. 7 is an illustration of a cross-section an example of high voltage switches integrated into two die and stacked.

FIG. 7 is an illustration of a cross-section an example of the switches integrated into two die and stacked. The top switches (e.g., switches 305A and 305B in FIG. 3, switches 405A, 405B, and 405C in FIG. 4, or switches 505A, 505B, and 505C in FIG. 5) are formed on a shared first die or first IC 735. The bottom switches (e.g., switches 310B and 310A in FIG. 3, switches 405D, 405E, and 405F in FIG. 4, or switches 505D, 505E, and 505F in FIG. 5) are formed on a shared second IC 740. The first IC is stacked substantially superjacent to the second IC 740. In the example shown, each die includes three switches that are used to form the output bridge circuit of FIG. 5. Because each of the ICs contains three switches, there is less opportunity for alignment problems in forming the stacked bridge circuit than if each individual top switch is packaged as an individual IC and stacked on an individual packaged bottom switch IC.

The cathode of the first top switch 705A is coupled to the anode of the first bottom switch 705D to form a first circuit node. The first node is to be communicatively coupled to an electrode to provide therapy to the right atrium (RAC). The cathode of the second top switch 705B is coupled to the anode of the second bottom switch 705E to form a second circuit node. The second node is to be communicatively coupled to an electrode to provide therapy to the right ventricle (RVC). The cathode of the third top switch 705C is coupled to the anode of the third bottom switch 705D to form a third circuit node. The third node is to be communicatively coupled to an electrode formed on the can of the device (CAN).

The anodes of the top switches are attached to a connection to the high voltage generated in the device and the cathodes of the bottom switches are connected to ground. In certain examples, the gate connection of the top switches is connected to a switch (not shown in the Figure) to enable the top switch. In certain examples, the enabling switches are FETs.

According to some examples, one die may be formed for each connection to a defibrillation electrode. For the output bridge circuit 300 in FIG. 3, switches 305A and 310B are formed on a first die for the connection to the atrial coil 316, and switches 305B and 310A are formed on a second die for the connection to the ventricular coil 318. Access to interconnect to form the bridge circuit 300 is available at the outside of the die packages. For the output bridge circuit 500 in FIG. 5, switches 505A and 505D are formed on a first die for the connection to the right atrial electrode 516, switches 505B and 505E are formed on a second die for the connection to the right ventricular electrode 518, and switches 505C and 505F are formed on a third die for the connection to the can electrode 530.

In some examples, the switches are formed into a single die. However, this may be more difficult to implement because of interconnect required by the circuit configuration and because of the multiple voltages involved.

Returning to FIG. 4, a switching circuit implements switch 405G. In certain examples the switching circuit includes an insulating gate npn bipolar transistor (IGBT) coupled between node 402 and node 404. Node 402 is a common node of switches 405A, 405B, and 405C, and node 404 is a node of the therapy energy source (e.g., the HV Cap). Activating the IGBT provides therapy energy to the output bridge circuit. In certain examples, the switching circuit includes an enable circuit coupled to the IGBT. Descriptions of switching circuits to provide defibrillation or cardioversion therapy energy to output bridge circuits such as those in FIGS. 3, 4, and 5, may be found in Linder et al., "Defibrillation Shock Output Circuit," patent application Ser. No. 12/332,497, filed Dec. 11, 2008, which is incorporated herein by reference in its entirety.

The configuration described above with respect to FIGS. 4 and 5 also provides all solid state control for performing the switching (without requiring any optocoupler, triggering transformer, floating supply, or transformer-coupled supply, as may be required by certain other approaches). This can reduce expense, circuit volume, and complications that may arise from such other approaches.

The configurations described above with respect to FIGS. 4 and 5 also have advantages over hard-wired "hot can" or "cold can" configurations described above since it allows flexibility in defibrillation waveforms. For example, Table 1 illustrates a shock vector from RV coil to RA coil by closing switches 405A, 405E, and 405G during phase 1, and then closing switches 405B, 405D, and 405G during phase 2. In another example, the polarity of this shock vector could be reversed by closing switches 405B, 405D, and 405G during phase 1, and then closing switches 405A, 405E, and 405G during phase 2. Similarly, the other waveform polarities can also be reversed by interchanging the switches closed in phase 1 with the switches closed in phase 2.

In a further example, automatic polarity reversal is implemented. For example, after each shock delivery, sensing circuits are used to determine whether the rhythm has successfully been converted from a tachyarrhythmia or fibrillation waveform to a normal waveform. If, after a specified number of attempts (e.g., 3 shocks), the heart has not been converted to a normal rhythm, then at least one subsequent attempt (e.g., the 4th shock) is performed using the opposite waveform polarity of the same shock vector. In other examples, different shock vectors or polarities are automatically used, such as when initial defibrillation shock attempts for that particular episode have been unsuccessful at obtaining a normal heart rhythm.

Implementing the configurations by integrating the high voltage switches results in better use of circuit area, ultimately allowing an IMD to be made smaller, thereby improving patient comfort. And because integrating the switches results in higher yield of the switch devices, the integrating reduces the cost of implementing the configurations.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a cardioversion or defibrillation therapy energy source coupled to a first node;
    a bridge circuit coupled to the first node and a second node, wherein the bridge circuit includes:
        a first switch coupled to the first node and a third node, wherein the third node is configured to be communicatively coupled to a first implantable electrode sized and shaped for defibrillation or cardioversion therapy;
        a second switch coupled to the first node and a fourth node, wherein the fourth node is configured to be communicatively coupled to a second implantable electrode sized and shaped for defibrillation or cardioversion therapy;
        a third switch coupled to the third node and the second node;
        a fourth switch coupled to the fourth node and the second node; and
        a first integrated circuit and a second integrated circuit, wherein the first and second switches are included in the first integrated circuit and have adjacent and non-adjacent edges, and the third and fourth switches are included in the second integrated circuit and have adjacent and non-adjacent edges, wherein high voltage electrical isolation structures are disposed between adjacent edges and at non-adjacent edges of the of the first and second switches and are disposed between adjacent edges and at non-adjacent edges of the third and fourth switches, and wherein the isolation structures between the adjacent edges are formed thinner than the isolation structures formed at the non-adjacent edges, and
        wherein the second integrated circuit is stacked substantially superjacent to the first integrated circuit such that a cathode of the first switch is coupled to an anode of the third switch and a cathode of the second switch is coupled to an anode of the fourth switch.

2. The apparatus of claim 1, wherein the isolation structures at the non-adjacent edges include a thickness sufficient to accommodate sawing of the first and second integrated circuits.

3. The apparatus of claim 2, wherein the isolation structures include aluminum column diffusion isolation structures.

4. The apparatus of claim 1, wherein one or more of the isolation structures include insulative material in deep reactive ion etched trenches.

5. The apparatus of claim 1, wherein the energy source includes a capacitor, and wherein the first and second switches include remote gate thyristors (RGTs) and the third and fourth switches include silicon controlled rectifiers (SCRs).

6. The apparatus of claim 1, including:
    a fifth switch coupled to the first node and a fifth node, wherein the fifth node is configured to be communicatively coupled to a third implantable electrode sized and shaped for defibrillation or cardioversion therapy; and
    a sixth switch coupled to the fifth node and the second node, wherein the fifth switch is included in the first integrated circuit and the sixth switch is included in the second integrated circuit.

7. The apparatus of claim 6, including the first implantable electrode and the second implantable electrode, wherein the first implantable electrode is configured for placement in or near an atrium, the second implantable electrode is configured for placement in or near a ventricle; and the third implantable electrode includes an electrode formed on a housing of the apparatus.

8. The apparatus of claim 7, wherein the second implantable electrode is configured for placement in or near a left ventricle.

9. The apparatus of claim 6, including first, second, and third field effect transistors (FETs), wherein the first, second, and fifth switches include a gate connection, and wherein the gate connections are coupled to the first, second, and third FETs, respectively.

10. The apparatus of claim 1, including a seventh switch coupled between the therapy energy source and the first node, wherein the seventh switch provides the therapy energy to the bridge circuit.

11. The apparatus of claim 10, wherein the seventh switch includes an insulated gate bipolar transistor (IGBT), and wherein the apparatus includes an enable circuit coupled to the IGBT.

12. A method comprising:
    forming a bridge circuit by forming a first switch and a second switch in a first integrated circuit and forming a third switch and a fourth switch in a second integrated circuit, wherein the first and second switches have an adjacent edge and non-adjacent edges, and wherein the third and fourth switches have an adjacent edge and a non-adjacent edge;
    forming high voltage electrical isolation structures in the first and second integrated circuits between adjacent edges of the switches and at non-adjacent edges of the switches, such that the isolation structures between the adjacent edges are thinner than isolation structures formed at the non-adjacent edges;
    stacking the first integrated circuit substantially superjacent to the second integrated circuit;

coupling a cathode of the first switch to an anode of the third switch and coupling a cathode of the second switch to an anode of the fourth switch;

coupling a first node to the cathode of the first switch, wherein the first node is configured to be communicatively coupled to a first implantable electrode sized and shaped for defibrillation or cardioversion therapy;

coupling a second node to the cathode of the second switch, wherein the second node is configured to be communicatively coupled to a second implantable electrode sized and shaped for defibrillation or cardioversion therapy;

coupling the anodes of the first and second switches to a third node; and coupling a cardioversion or defibrillation therapy energy source to the third node.

13. The method of claim 12, wherein forming isolation structures at the non-adjacent edges includes forming isolation structures at the non-adjacent edges that are wide enough to accommodate sawing of the first and second integrated circuits.

14. The method of claim 13, wherein forming isolation structures includes forming isolation structures using aluminum column diffusion.

15. The method of claim 12, wherein forming isolation structures includes forming isolation structures using deep reactive ion etching.

16. The method of claim 12,
wherein coupling the energy source includes coupling a capacitor to the third node, wherein the capacitor is configured to store sufficient charge to provide the cardioversion or defibrillation therapy, and
wherein stacking first and second integrated circuits includes stacking a first integrated circuit including remote gate thyristors (RGTs) and stacking a second integrated circuit including silicon controlled rectifiers (SCRs).

17. The method of claim 12, including:
coupling a cathode of a fifth switch to an anode of a sixth switch, wherein the fifth switch is included in the first integrated circuit and the sixth switch is included in the second integrated circuit; and
coupling a fourth node to the cathode of the fifth switch, wherein the fourth node is configured to be communicatively coupled to a third implantable electrode sized and shaped for defibrillation or cardioversion therapy.

18. The method of claim 17,
wherein coupling a first node to the cathode of the first switch includes coupling the cathode of the first switch to a node to be communicatively coupled to a first implantable electrode sized and shaped for placement in or near an atrium;

wherein coupling a second node to the cathode of the second switch includes coupling the cathode of the second switch to a node to be communicatively coupled to a second implantable electrode sized and shaped for placement in or near a ventricle; and wherein coupling a fourth node to the cathode of the fifth switch includes coupling the cathode to a node to be communicatively coupled to an electrode formed on a housing of the apparatus.

19. The method of claim 12, including coupling a seventh switch between the therapy energy source and the third node to control delivery of therapy energy to the third node.

20. An apparatus comprising:
a cardioversion or defibrillation therapy energy source coupled to a first node;
a bridge circuit coupled to the first node and a second node, wherein the bridge circuit includes:
a first high voltage switch coupled to the first node and a third node, wherein the third node is configured to be communicatively coupled to a first implantable electrode sized and shaped for defibrillation or cardioversion therapy;
a second high voltage switch coupled to the first node and a fourth node, wherein the fourth node is configured to be communicatively coupled to a second implantable electrode sized and shaped for defibrillation or cardioversion therapy;
a third high voltage switch coupled to the third node and the second node; and
a fourth high voltage switch coupled to the fourth node and the second node, wherein the first, second, third, and fourth high voltage switches are formed on a single shared integrated circuit such that a cathode of the first high voltage switch is coupled to an anode of the third high voltage switch and a cathode of the second high voltage switch is coupled to an anode of the fourth high voltage switch, and wherein the integrated circuit includes high voltage electrical isolation structures between adjacent edges of the high voltage switches and at non-adjacent edges of the high voltage switches, and wherein the isolation structures between the adjacent edges are thinner than the isolation structures at the non-adjacent edges.

21. The apparatus of claim 20, wherein the isolation structures are formed using aluminum column diffusion, and wherein the isolation structures at the non-adjacent edges include a thickness sufficient to accommodate sawing of the integrated circuit.

22. The apparatus of claim 20, wherein the isolation structures are formed using deep reactive ion etching.

* * * * *